United States Patent [19]

Morinaka et al.

[11] Patent Number: 4,990,619

[45] Date of Patent: Feb. 5, 1991

[54] PYRAZOLINE DERIVATIVES

[75] Inventors: Yasuhiro Morinaka, Tsuchiura; Hiroyoshi Nishi, Ibaraki; Toshiaki Watanabe, Yokohama; Satoshi Yuki, Sendai; Hiroko Sakurai, Yokohama; Yoshio Hayashi, Ushiku; Nobuko Fukushima, Hachioji, all of Japan

[73] Assignee: Mitsubishi Kasei Corporation, Tokyo, Japan

[21] Appl. No.: 451,526

[22] Filed: Dec. 18, 1989

Related U.S. Application Data

[62] Division of Ser. No. 123,237, Nov. 20, 1987, Pat. No. 4,906,644.

[30] Foreign Application Priority Data

Nov. 20, 1986 [JP] Japan ................................ 61-277363
Nov. 20, 1986 [JP] Japan ................................ 61-277364

[51] Int. Cl.$^5$ ............................................. C07D 401/14
[52] U.S. Cl. .................................... 546/256; 548/362; 548/374
[58] Field of Search ................. 546/256; 548/362, 374

[56] References Cited

FOREIGN PATENT DOCUMENTS 1445931 2/1969 Fed. Rep. of Germany .
2555353 6/1976 Fed. Rep. of Germany .
45-10148 4/1970 Japan .
45-26736 11/1970 Japan .

OTHER PUBLICATIONS

Chemical Abstracts vol. 86 (1977), Abst. No. 89683w to Cherkesova et al.
Chemical Abstracts, vol. 93 (1980), Abst. No. 8079y to Kharchenko et al.
Disseratationes Pharmaceuticae et Pharmacologicae, 1966, XVIII, 4, pp. 345-350.
Chemical Abstracts, vol. 46, 8082-8083 (1952), Abstract of Linares et al, Pubs. Inst. Quim., "Alonso Barba" (Madrid) 4, 310-15 (1950).

Primary Examiner—Joseph Paul Brust
Assistant Examiner—Jacqueline Haley
Attorney, Agent, or Firm—Oblon, Spivak, McClelland, Maier & Neustadt

[57] ABSTRACT

A lipid-peroxide formation inhibitor useful as a preventive medicine and/or therapeutic medicine against various ischemic diseases and accompanying diseases such as various brain diseases, heart diseases and peripheral circulatory diseases and novel pyrazolone derivatives having such inhibitory activity and their pharmaceutically acceptable salts.

1 Claim, No Drawings

PYRAZOLINE DERIVATIVES

This is a division of application Ser. No. 07/123,237, filed on Nov. 20, 1987, U.S. Pat. No. 4,906,644.

DETAILED DESCRIPTION OF THE INVENTION

A. Industrial Field of the Invention

The present invention relates to a lipid-peroxide formation inhibiting composition and novel pyrazolone derivatives and their salts which may be the active ingredient of such inhibiting compositions, and more particularly relates to a lipid-peroxide formation inhibiting composition useful as a preventive medicine and/or therapeutic medicine against various ischemic diseases and various diseases resulting therefrom such as various brain diseases, heart diseases and peripheral circulatory diseases and novel pyrazolone derivatives having such inhibiting activity and their pharmaceutically acceptable salts.

B. Prior Art and Problems Thereof

With respect to circulatory disturbances and diseases in brain, heart and periphery, ischemia (the phenonena wherein blood is not fed to tissue) causes lipid-peroxide formation by the action of the active oxygen species (HO radical, superoxide, etc.) which is formed in the peripheral tissue. It is known that such change not only proceeds during the ischemic period but also is accelerated by the reoxidation through blood reflow, and causes further damage to the cell membrane which is rich in unsaturated fatty acids, damage to the central and peripheral tissue and vascular endothelium damage, vascular contraction or tissue edema, etc., resulting in further proceeding with the morbid state on account of the series of vicious circle ("Cerebral ischemia and cell disturbance" edited by Takao Asano, Nyuron Co., Ltd., 1980; "Cerebral ischemia and free radical" edited by Takao Asano, Nyuron Co., Ltd., 1983).

Therefore, if the formation of lipid-peroxide due to active oxygen species is inhibited or scavenged, it becomes possible to prevent the tissue and vascular endothelium damage, vascular contraction and tissue edema, etc. and to realize a novel preventive medicine and/or therapeutic medicine which acts against the cause of disease and completely differs from the traditional drugs which are directed to circulatory improvement by blood flow increase. Particularly in recent years, the treatments of increasing blood flow in the brain is doubted in effectiveness and sometimes said to exert disadvantageous influence in the acute phase of cerebral vascular disorders. Such being the case, much importance is placed on the development of novel medicine as described above.

The pharmaceuticals that are known to inhibit lipid peroxidation due to active oxygen species include vitamin E, Idebenon (Biochemical and Biophysical Research Communications, 125, 1046 (1984); Journal of Takeda Research Laboratories 44, 30 (1985) as expressed by the following formula:

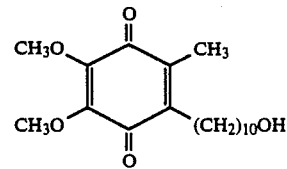

and nizofenone (Journal of Neurochemistry, 37, 934 (1981)) as expressed by the following formula:

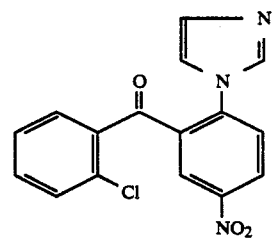

However, vitamin E is not sufficient to inhibiting lipid peroxidation. Both idebenon and nizofenone require prolonged synthesis process. In addition, idebenon is difficult to dissolve in water, causing trouble in preparing injectable formulas. Nizofenone is defective in depressing the central nervous system (IYAKUHIN KENKYU, 16, 1 (1985)).

A variety of pyrazolone derivatives are already known.

Japanese Patent Publications sho 45 (1970)-10148 and sho 45 (1970)-26736 disclose the derivatives of 3-pyridylpyrazolin-5-one as expressed by the following formula A:

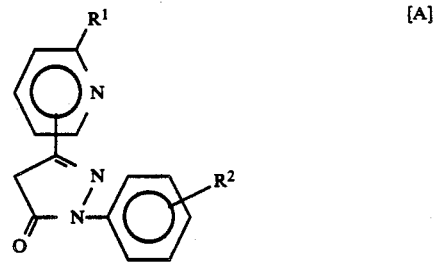

wherein $R^1$ is a hydrogen atom (H) or methyl group and $R^2$ is hydrogen atom (H) or a substituent, said derivatives being used as analgesics or antispasmodics. In addition, Diss. Pharm. Pharmacol., 18 (4) 345 (1966) discloses the compound as expressed by the following formula B:

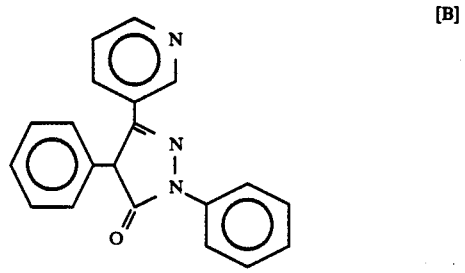

said compound being used as an antiphlogistic. There is, however, no description relating to the inhibition of lipid peroxidation by active oxygen species.

Pubs. inst. quim., "Alonso Barba" (Madrid) 4, 310 (1950) (Chemical Abstracts, vol. 46, 8082 (1952)) discloses the compound as expressed by the following formula C:

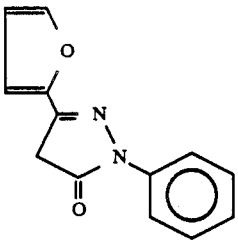

[C]

said compound being related to phytohormone function, there is no description regarding pharmacological action.

C. Means for Solving the Above-mentioned Problems

Our intensive research and study for the purpose of providing useful medicines capable of inhibiting lipid-peroxide formation due to active oxygen species led to the finding that strong inhibiting function against lipid-peroxide formation as well as protective function such as the restoration of abnormal electroencephalogram in an animal model close to an actual morbid state in the resumption condition of cerebral ischemia are exhibited by a pyrazolone derivative or pharmaceutically acceptable salts thereof, said derivative being expressed by the following general formula (I):

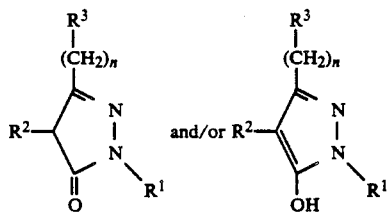

(I)

wherein $R^1$ is a cycloalkyl group, an aryl group which may contain substituent/s or a heterocyclic group, $R^2$ is hydrogen atom or an alkyl group, $R^3$ is a heterocyclic group and n is zero or one.

The lipid-peroxide formation inhibiting composition of the present invention comprises as the active ingredient at least one of the pyrazolone derivatives which are of the keto form expressed by the following general formula (I') and/or of the enol form expressed by another general formula (I''):

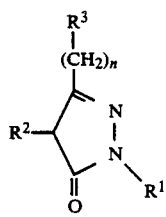

(I')

-continued (I'')

and pharmaceutical acceptable salts thereof. In the above formulae, $R^1$ is a cycloalkyl group of from 5 to 7 carbon atoms such as cyclopentyl group, cyclohexyl group, cycloheptyl group, etc.; an aryl group such as phenyl group, naphthyl group, etc., which can each contain substituent/s; or a heterocyclic group such as pyridyl group, pyrimidyl group, pyridazinyl group, benzothiazolyl group, etc.

The substitutents for the aryl group include alkyl groups of from 1 to 5 carbon atoms such as methyl group, ethyl group, propyl group, isopropyl group, butyl group, isobutyl group, sec-butyl group, tert-butyl group, pentyl group, etc.; alkoxy groups of from 1 to 5 carbon atoms such as methoxy group, ethoxy group, propoxy group, isopropoxy group, butoxy group, pentyloxy group, etc.; halogen atoms such as chlorine atom, etc.; alkoxycarbonyl groups of from 2 to 5 total carbon atoms such as methoxycarbonyl group, ethoxycarbonyl group, propoxycarbonyl group, butoxycarbonyl group, etc.; carboxy group; alkoxycarbonylalkyl groups such as alkoxycarbonylmethyl groups of from 3 to 6 total carbon atoms; carboxyalkyl groups such as carboxymethyl group; alkylmercapto groups of from 1 to 3 carbon atoms such as methylmercapto group, ethylmercapto group, propylmercapto group; trifluoromethyl group; hydroxyl group and the like.

$R^2$ represents a hydrogen atom (H) or an alkyl group of from 1 to 5 carbon atoms.

$R^3$ represents a heterocyclic group such a pyridyl group, a furanyl group, an imidazolyl group, etc.

n represents zero (0) or one (1).

In the compounds of the present invention, it is preferable that $R^1$ is a cyclohexyl group, a phenyl group, a 4-methylphenyl group, a 4-ethylphenyl group, a 4-methoxyphenyl group, a 4-ethoxyphenyl group or a 4-chlorophenyl group, $R^2$ is a hydrogen atom (H), a methyl group, an ethyl group or a propyl group, and $R^3$ is pyridyl group or a furanyl group, and is particularly preferable that the compounds include a 4-methylphenyl group or a 4-chlorophenyl group as $R^1$, a hydrogen atom (H), a methyl group, an ethyl group or a propyl group as $R^2$, and a pyridyl group as $R^3$.

Specific examples of the pyrazolone derivatives used in the compositions of the present invention include the followings:

(1) 1-Phenyl-3-(3-pyridyl)-2-pyrazolin-5-one,
(2) 1-(4-Methylphenyl)-3-(3-pyridyl)-2-pyrazolin-5-one,
(3) 1-(3-Methylphenyl)-3-(3-pyridyl)-2-pyrazolin-5-one,
(4) 1-(2-Methylphenyl)-3-(3-pyridyl)-2-pyrazolin-5-one,
(5) 1-(4-Ethylphenyl)-3-(3-pyridyl)-2-pyrazolin-5-one,
(6) 1-(4-Propylphenyl)-3-(3-pyridyl)-2-pyrazolin-5-one,
(7) 1-(4-Butylphenyl)-3-(3-pyridyl)-2-pyrazolin-5-one,
(8) 1-(4-Pentylphenyl)-3-(3-pyridyl)-2-pyrazolin-5-one,
(9) 1-(3,4-Dimethylphenyl)-3-(3-pyridyl)-2-pyrazolin-5-one,
(10) 1-(4-Methoxyphenyl)-3-(3-pyridyl)-2-pyrazolin-5-one,

(11) 1-(3-Methoxyphenyl)-3-(3-pyridyl)-2-pyrazolin-5-one,
(12) 1-(2-Methoxyphenyl)-3-(3-pyridyl)-2-pyrazolin-5-one,
(13) 1-(4-Ethoxyphenyl)-3-(3-pyridyl)-2-pyrazolin-5-one,
(14) 1-(4-Propoxyphenyl)-3-(3-pyridyl)-2-pyrazolin-5-one,
(15) 1-(4-Butoxyphenyl)-3-(3-pyridyl)-2-pyrazolin-5-one,
(16) 1-(4-Pentoxyphenyl)-3-(3-pyridyl)-2-pyrazolin-5-one,
(17) 1-(3,4-Dimethoxyphenyl)-3-(3-pyridyl)-2-pyrazolin-5-one,
(18) 1-(4-Chlorophenyl)-3-(3-pyridyl)-2-pyrazolin-5-one,
(19) 1-(3-Chlorophenyl)-3-(3-pyridyl)-2-pyrazolin-5-one,
(19a) 1-(3-Chlorophenyl)-4-methyl-3-(3-pyridyl)-2-pyrazolin-5-one,
(20) 1-(4-Bromophenyl)-3-(3-pyridyl)-2-pyrazolin-5-one,
(21) 1-(4-Fluorophenyl)-3-(3-pyridyl)-2-pyrazolin-5-one,
(22) 1-(3-Chloro-4-methylphenyl)-3-(3-pyridyl)-2-pyrazolin-5-one,
(23) 1-(3-Trifluoromethylphenyl)-3-(3-pyridyl)-2-pyrazolin-5-one,
(24) 1-(4-Trifluoromethylphenyl)-3-(3-pyridyl)-2-pyrazolin-5-one,
(25) 1-(4-Methoxycarbonylphenyl)-3-(3-pyridyl)-2-pyrazolin-5-one,
(26) 1-(4-Ethoxycarbonylphenyl)-3-(3-pyridyl)-2-pyrazolin-5-one,
(26a) 4-[4-Methyl-3-(3-pyridyl)-5-oxo-2-pyrazolin-1-yl]benzoic acid,
(27) 4-[3-(3-Pyridyl)-5-oxo-2-pyrazolin-1-yl]benzoic acid,
(28) 1-(4-Ethoxycarbonylmethylphenyl)-3-(3-pyridyl)-2-pyrazolin-5-one,
(28a) 1-(4-Ethoxycarbonylmethylphenyl)-4-methyl-3-(3-pyridyl)-2-pyrazolin-5-one,
(29) 4-[3-(3-Pyridyl)-5-oxo-2-pyrazolin-1-yl]phenylacetic acid,
(29a) 4-[4-Methyl-3-(3-pyridyl)-5-oxo-2-pyrazolin-1-yl]phenylacetic acid,
(30) 1-(4-Methylthiophenyl)-3-(3-pyridyl)-2-pyrazolin-5-one,
(31) 1-(3-Methylthiophenyl)-3-(3-pyridyl)-2-pyrazolin-5-one,
(32) 1-(4-Hydroxyphenyl)-3-(3-pyridyl)-2-pyrazolin-5-one,
(33) 1-(3-Hydroxyphenyl)-3-(3-pyridyl)-2-pyrazolin-5-one,
(34) 1-(3,4-Dihydroxyphenyl)-3-(3-pyridyl)-2-pyrazolin-5-one,
(35) 1-(3,4,5-Trimethylphenyl)-3-(3-pyridyl)-2-pyrazolin-5-one,
(35a) 1-(3,4,5-Trimethylphenyl)-4-methyl-3-(3-pyridyl)-2-pyrazolin-5-one,
(36) 1-(α-Naphthyl)-3-(3-pyridyl)-2-pyrazolin-5-one,
(36a) 4-Methyl-1-(α-naphthyl)-3-(3-pyridyl)-2-pyrazolin-5-one,
(37) 1-Cyclohexyl-3-(3-pyridyl)-2-pyrazolin-5-one,
(38) 1-Cyclopentyl-3-(3-pyridyl)-2-pyrazolin-5-one,
(38a) 1-Cyclopentyl-4-methyl-3-(3-pyridyl)-2-pyrazolin-5-one,
(39) 1-Cycloheptyl-3-(3-pyridyl)-2-pyrazolin-5-one,
(39a) 1-Cycloheptyl-4-methyl-3-(3-pyridyl)-2-pyrazolin-5-one,
(40) 1-(2-Pyridyl)-3-(3-pyridyl)-2-pyrazolin-5-one,
(41) 1-(4-Pyridyl)-3-(3-pyridyl)-2-pyrazolin-5-one,
(42) 1-(2-Pyrazinyl)-3-(3-pyridyl)-2-pyrazolin-5-one,
(42a) 1-(2-Benzothiazolyl)-4-methyl-3-(3-pyridyl)-2-pyrazolin-5-one,
(43) 3-(3-Pyridyl)-1-(2-pyrimidyl)-2-pyrazolin-5-one,
(44) 1-(3-Pyridazinyl)-3-(3-pyridyl)-2-pyrazolin-5-one,
(45) 1-(2-Benzothiazolyl)-3-(3-pyridyl)-2-pyrazolin-5-one,
(46) 1-Phenyl-3-(2-pyridyl)-2-pyrazolin-5-one,
(47) 1-Phenyl-3-(4-pyridyl)-2-pyrazolin-5-one,
(48) 4-Methyl-1-phenyl-3-(3-pyridyl)-2-pyrazolin-5-one,
(48a) 4-Methyl-1-phenyl-3-(2-pyridyl)-2-pyrazolin-5-one,
(48b) 4-Methyl-1-phenyl-3-(4-pyridyl)-2-pyrazolin-5-one,
(49) 4-Methyl-1-(4-methylphenyl)-3-(3-pyridyl)-2-pyrazolin-5-one,
(50) 4-Methyl-1-(3-methylphenyl)-3-(3-pyridyl)-2-pyrazolin-5-one,
(50a) 4-Methyl-1-(4-propoxyphenyl)-3-(3-pyridyl)-2-pyrazolin-5-one,
(51) 1-(4-Ethylphenyl)-4-methyl-3-(3-pyridyl)-2-pyrazolin-5-one,
(52) 4-Methyl-1-(4-propylphenyl)-3-(3-pyridyl)-2-pyrazolin-5-one,
(52a) 4-Methyl-1-(4-pentylphenyl)-3-(3-pyridyl)-2-pyrazolin-5-one,
(53) 1-(4-Butylphenyl)-4-methyl-3-(3-pyridyl)-2-pyrazolin-5-one,
(54) 1-(3,4-Dimethylphenyl)-4-methyl-3-(3-pyridyl)-2-pyrazolin-5-one,
(55) 1-(4-Methoxyphenyl)-4-methyl-3-(3-pyridyl)-2-pyrazolin-5-one,
(56) 1-(3-Methoxyphenyl)-4-methyl-3-(3-pyridyl)-2-pyrazolin-5-one,
(57) 1-(4-Ethoxyphenyl)-4-methyl-3-(3-pyridyl)-2-pyrazolin-5-one,
(58) 1-(4-Butoxyphenyl)-4-methyl-3-(3-pyridyl)-2-pyrazolin-5-one,
(59) 1-(3,4-Dimethoxyphenyl)-4-methyl-3-(3-pyridyl)-2-pyrazolin-5-one,
(59a) 1-(3,4-Dihydroxyphenyl)-4-methyl-3-(3-pyridyl)-2-pyrazolin-5-one,
(60) 1-(4-Chlorophenyl)-4-methyl-3-(3-pyridyl)-2-pyrazolin-5-one,
(60a) 1-(3-Chloro-4-methylphenyl)-4-methyl-3-(3-pyridyl)-2-pyrazolin-5-one,
(61) 1-(4-Fluorophenyl)-4-methyl-3-(3-pyridyl)-2-pyrazolin-5-one,
(61a) 1-(3,4-Dichlorophenyl)-4-methyl-3-(3-pyridyl)-2-pyrazolin-5-one,
(62) 4-Methyl-1-(4-methylthiophenyl)-3-(3-pyridyl)-2-pyrazolin-5-one,
(63) 1-(4-Trifluoromethylphenyl)-4-methyl-3-(3-pyridyl)-2-pyrazolin-5-one,
(64) 1-(4-Hydroxyphenyl)-4-methyl-3-(3-pyridyl)-2-pyrazolin-5-one,
(65) 1-Cyclohexyl-4-methyl-3-(3-pyridyl)-2-pyrazolin-5-one,
(66) 4-Methyl-1-(2-pyridyl)-3-(3-pyridyl)-2-pyrazolin-5-one,
(66a) 4-Methyl-1-(2-pyrazinyl)-3-(3-pyridyl)-2-pyrazolin-5-one, (66b) 4-Methyl-3-(3-pyridyl)-1-(2-pyrimidyl)-2-pyrazolin-5-one,
(66c) 4-Methyl-1-(3-pyridazinyl)-3-(3-pyridyl)-2-pyrazolin-5-one,
(66d) 4-Methyl-1-(4-pyridyl)-3-(3-pyridyl)-2-pyrazolin-5-one,
(67) 4-Ethyl-1-phenyl-3-(3-pyridyl)-2-pyrazolin-5-one,
(68) 4-Ethyl-1-(4-methylphenyl)-3-(3-pyridyl)-2-pyrazolin-5-one,
(69) 4-Ethyl-1-(4-ethylphenyl)-3-(3-pyridyl)-2-pyrazolin-5-one,
(70) 1-(4-Butylphenyl)-4-ethyl-3-(3-pyridyl)-2-pyrazolin-5-one,
(71) 4-Ethyl-1-(3,4-dimethylphenyl)-3-(3-pyridyl)-2-pyrazolin-5-one,
(72) 4-Ethyl-1-(4-methoxyphenyl)-3-(3-pyridyl)-2-pyrazolin-5-one,
(73) 1-(4-Ethoxyphenyl)-4-ethyl-3-(3-pyridyl)-2-pyrazolin-5-one,
(74) 1-(4-Chlorophenyl)-4-ethyl-3-(3-pyridyl)-2-pyrazolin-5-one,
(75) 1-Cyclohexyl-4-ethyl-3-(3-pyridyl)-2-pyrazolin-5-one,
(76) 4-Ethyl-1-(2-pyridyl)-3-(3-pyridyl)-2-pyrazolin-5one,
(76a) 1-Phenyl-4-propyl-3-(3-pyridyl)-2-pyrazolin-5-one,
(77) 1-(4-Methylphenyl)-4-propyl-3-(3-pyridyl)-2-pyrazolin-5-one,
(78) 1-(4-Ethylphenyl)-4-propyl-3-(3-pyridyl)-2-pyrazolin-5-one,
(79) 1-(4-Methoxyphenyl)-4-propyl-3-(3-pyridyl)-2-pyrazolin-5-one,
(80) 1-(4-Ethoxyphenyl)-4-propyl-3-(3-pyridyl)-2-pyrazolin-5-one,
(81) 1-(4-Chlorophenyl)-4-propyl-3-(3-pyridyl)-2-pyrazolin-5-one,
(82) 1-Cyclohexyl-4-propyl-3-(3-pyridyl)-2-pyrazolin-5-one,
(82a) 4-Butyl-1-phenyl-3-(3-pyridyl)-2-pyrazolin-5-one,
(83) 1-Phenyl-3-(3-pyridylmethyl)-2-pyrazolin-5-one,
(84) 1-(4-Methylphenyl)-3-(3-pyridylmethyl)-2-pyrazolin-5one,
(85) 1-(3-Methylphenyl)-3-(3-pyridylmethyl)-2-pyrazolin-5one,
(86) 1-(2-Methylphenyl)-3-(3-pyridylmethyl)-2-pyrazolin-5one,
(87) 1-(4-Ethylphenyl)-3-(3-pyridylmethyl)-2-pyrazolin-5-one,
(88) 1-(4-Propylphenyl)-3-(3-pyridylmethyl)-2-pyrazolin-5-one,
(89) 1-(4-Butylphenyl)-3-(3-pyridylmethyl)-2-pyrazolin-5-one,
(90) 1-(3,4-Dimethylphenyl)-3-(3-pyridylmethyl)-2-pyrazolin-5-one,
(91) 1-(4-Methoxyphenyl)-3-(3-pyridylmethyl)-2-pyrazolin-5-one,
(92) 1-(3-Methoxyphenyl)-3-(3-pyridylmethyl)-2-pyrazolin-5-one,
(93) 1-(4-Ethoxyphenyl)-3-(3-pyridylmethyl)-2-pyrazolin-5-one,
(94) 1-(4-Butoxyphenyl)-3-(3-pyridylmethyl)-2-pyrazolin-5-one,
(95) 1-(3,4-Dimethoxyphenyl)-3-(3-pyridylmethyl)-2-pyrazolin-5-one,
(96) 1-(4-Chlorophenyl)-3-(3-pyridylmethyl)-2-pyrazolin-5-one,
(97) 1-(4-Fluorophenyl)-3-(3-pyridylmethyl)-2-pyrazolin-5-one,
(98) 1-(4-Trifluoromethylphenyl)-3-(3-pyridylmethyl)-2-pyrazolin-5-one,
(99) 1-(4-Methylthiophenyl)-3-(3-pyridylmethyl)-2-pyrazolin-5-one,
(100) 4-[3-(3-pyridylmethyl)-5-oxo-2-pyrazolin-1-yl]benzoic acid,
(101) 1-(4-Hydroxyphenyl)-3-(3-pyridylmethyl)-2-pyrazolin-5-one,
(102) 1-(α-Naphthyl)-3-(3-pyridylmethyl)-2-pyrazolin-5-one,
(103) 1-Cyclohexyl-3-(3-pyridylmethyl)-2-pyrazolin-5-one,
(104) 1-(2-Pyridyl)-3-(3-pyridylmethyl)-2-pyrazolin-5-one,
(105) 1-Phenyl-3-(2-pyridylmethyl)-2-pyrazolin-5-one,
(106) 1-(4-Methylphenyl)-3-(2-pyridylmethyl)-2-pyrazolin-5-one,
(107) 1-Phenyl-3-(4-pyridylmethyl)-2-pyrazolin-5-one,
(108) 3-(2-Furanyl)-1-phenyl-2-pyrazolin-5-one,
(109) 3-(2-Furanyl)-1-(4-methylphenyl)-2-pyrazolin-5-one,
(110) 3-(2-Furanyl)-1-(3-methylphenyl)-2-pyrazolin-5-one,
(111) 3-(2-Furanyl)-1-(2-methylphenyl)-2-pyrazolin-5-one,
(112) 1-(4-Ethylphenyl)-3-(2-furanyl)-2-pyrazolin-5-one,
(113) 1-(4-Butylphenyl)-3-(2-furanyl)-2-pyrazolin-5-one,
(114) 3-(2-Furanyl)-1-(3,4-dimethylphenyl)-2-pyrazolin-5-one,
(115) 3-(2-Furanyl)-1-(4-methoxyphenyl)-2-pyrazolin-5-one,
(116) 3-(2-Furanyl)-1-(3-methoxyphenyl)-2-pyrazolin-5-one,
(117) 1-(4-Ethoxyphenyl)-3-(2-furanyl)-2-pyrazolin-5-one,
(118) 1-(4-Butoxyphenyl)-3-(2-furanyl)-2-pyrazolin-5-one,
(119) 3-(2-Furanyl)-1-(3,4-dimethoxyphenyl)-2-pyrazolin-5-one,
(120) 1-(4-Chlorophenyl)-3-(2-furanyl)-2-pyrazolin-5-one,
(121) 1-(4-Fluorophenyl)-3-(2-furanyl)-2-pyrazolin-5-one,
(122) 3-(2-Furanyl)-1-(4-methylthiophenyl)-2-pyrazolin-5-one,
(123) 1-(4-Trifluoromethylphenyl)-3-(2-furanyl)-2-pyrazolin-5-one,
(124) 3-(2-Furanyl)-1-(4-hydroxyphenyl)-2-pyrazolin-5-one,
(125) 3-(2-Furanyl)-1-(α-naphthyl)-2-pyrazolin-5-one,
(126) 1-Cyclohexyl-3-(2-furanyl)-2-pyrazolin-5-one,
(127) 3-(2-Furanyl)-1-(2-pyridyl)-2-pyrazolin-5-one,
(128) 3-(1-Imidazolylmethyl)-1-phenyl-2-pyrazolin-5-one,
(129) 3-(1-Imidazolylmethyl)-1-(4-methylphenyl)-2-pyrazolin-5-one,
(130) 3-(1-Imidazolylmethyl)-1-(3-methylphenyl)-2-pyrazolin-5-one,
(131) 1-(4-Ethylphenyl)-3-(1-imidazolylmethyl)-2-pyrazolin-5-one,
(132) 1-(4-Butylphenyl)-3-(1-imidazolylmethyl)-2-pyrazolin-5-one,
(133) 3-(1-Imidazolylmethyl)-1-(3,4-dimethylphenyl)-2-pyrazolin-5-one, (134) 3-(1-Imidazolylmethyl)-1-(4-methoxyphenyl)-2-pyrazolin-5-one,
(135) 3-(1-Imidazolylmethyl)-1-(3-methoxyphenyl)-2-pyrazolin-5-one,
(136) 1-(4-Ethoxyphenyl)-3-(1-imidazolylmethyl)-2-pyrazolin-5-one,
(137) 1-(4-Butoxyphenyl)-3-(1-imidazolylmethyl)-2-pyrazolin-5-one,
(138) 1-(4-Chlorophenyl)-3-(1-imidazolylmethyl)-2-pyrazolin-5-one,
(139) 1-(4-Fluorophenyl)-3-(1-imidazolylmethyl)-2-pyrazolin-5-one,
(140) 1-(4-Hydroxyphenyl)-3-(1)-imidazolylmethyl)-2-pyrazolin-5-one,
(141) 3-(1-Imidazolylmethyl)-1-(α-naphthyl)-2-pyrazolin-5-one,
(142) 1-Cyclohexyl-3-(1-imidazolylmethyl)-2-pyrazolin-5-one,
(143) 3-(1-Imidazolylmethyl)-1-(2-pyridyl)-2-pyrazolin-5-one,
(144) 3-(1-Imidazolylmethyl)-4-methyl-1-phenyl-2-pyrazolin-5-one,
(145) 3-(1-Imidazolylmethyl)-4-methyl-1-(4-methylphenyl)-2-pyrazolin-5-one,
(146) 1-(4-Ethylphenyl)-3-(1-imidazolylmethyl)-4-methyl-2-pyrazolin-5-one,
(147) 1-(4-Butylphenyl)-3-(1-imidazolylmethyl)-4-methyl-2-pyrazolin-5-one,
(148) 1-(4-Chlorophenyl)-3-(1-imidazolylmethyl)-4-methyl-2-pyrazolin-5-one,
(149) 3-(1-Imidazolylmethyl)-1-(4-methoxyphenyl)-4-methyl-2-pyrazolin-5-one,
(150) 1-Cyclohexyl-3-(1-imidazolylmethyl)-4-methyl-2-pyrazolin-5-one,
(151) 3-(1-Imidazolylmethyl)-4-ethyl-1-(2-pyridyl)-2-pyrazolin-5-one,
(152) 4-Ethyl-3-(1-imidazolylmethyl)-1-phenyl-2-pyrazolin-5-one,
(153) 4-Ethyl-3-(1-imidazolylmethyl)-1-(4-methylphenyl)-2-pyrazolin-5-one,
(154) 1-(4-Butylphenyl)-4-ethyl-3-(1-imidazolylmethyl)-2-pyrazolin-5-one,
(155) 1-(4-Chlorophenyl)-4-ethyl-3-(1-imidazolylmethyl)-2-pyrazolin-5-one,
(156) 1-(3,4-Dichlorophenyl)-4-ethyl-3-(1-imidazolylmethyl)-2-pyrazolin-5-one,
(157) 4-Ethyl-3-(1-imidazolylmethyl)-1-(4-methoxyphenyl)-2-pyrazolin-5-one,
(158) 1-Cyclohexyl-3-(1-imidazolylmethyl)-2-pyrazolin-5-one,
(159) 3-(1-Imidazolylmethyl)-4-isopropyl-1-phenyl-2-pyrazolin-5-one,
(160) 1-(4-Chlorophenyl)-3-(1-imidazolylmethyl)-4-isopropyl-2-pyrazolin-5-one,
(161) 3-(1-Imidazolylmethyl)-4-isopropyl-1-(4-methylphenyl)-2-pyrazolin-5-one,
(162) 4-Butyl-3-(1-imidazolylmethyl)-1-phenyl-2-pyrazolin-5-one,
(163) 4-Butyl-3-(1-imidazolylmethyl)-1-(4-methylphenyl)-2-pyrazolin-5-one,
(164) 4-Butyl-3-(1-imidazolylmethyl)-1-(3-methylphenyl)-2-pyrazolin-5-one,
(165) 4-Butyl-1-(4-butylphenyl)-3-(1-imidazolylmethyl)-2-pyrazolin-5-one,
(166) 4-Butyl-1-(4-chlorophenyl)-3-(1-imidazolylmethyl)-2-pyrazolin-5-one,
(167) 4-Butyl-1-(3,4-dichlorophenyl)-3-(1-imidazolylmethyl)-2-pyrazolin-5-one,
(168) 4-Butyl-3-(1-imidazolylmethyl)-1-(4-methoxyphenyl)-2-pyrazolin-5-one,
(169) 4-Butyl-1-cyclohexyl-3-(1-imidazolylmethyl)-2-pyrazolin-5-one,
(170) 4-Butyl-3-(1-imidazolylmethyl)-1-(2-pyridyl)-2-pyrazolin-5-one,
(171) 1-(3,4-dichlorophenyl)-3-(1-imidazolylmethyl)-2-pyrazolin-5-one,
(172) 4-[3-(1-Imidazolylmethyl)-5-oxo-2-pyrazolin-1-yl]-phenylacetic acid,
(173) 4-[3-(1-Imidazolylmethyl)-5-oxo-2-pyrazolin-1-yl]-benzoic acid,
(174) 1-(4-Ethoxycarbonylmethylphenyl)-3-(1-imidazolylmethyl)-2-pyrazolin-5-one,
(175) 1-(4-Ethoxycarbonylphenyl)-3-(1-imidazolylmethyl)-2-pyrazolin-5-one.

Out of the above-listed compounds, Compounds (19a), (26), (26a), (28a), (29a), (35a), (36a), (38a), (39a), (42a), (48)–(107), and (109)–(175), for example, are novel, said compounds being expressed by the following general formula (Ia):

$$\text{(Ia)}$$

wherein $R^1$ represents a cycloalkyl group, a phenyl group which may contain substituent(s), or a pyridyl group, $R^2$ is a hydrogen atom (H) or an alkyl group, $R^3$ is a pyridyl, imidazolyl or furanyl group, and n is zero (0) or one (1), provided that, when n is zero and $R^3$ is a pyridyl group, $R^2$ represents an alkyl group, and when n is zero and $R^3$ is a furanyl group, $R^1$ represents a substituted phenyl group.

In other words, compounds of the general formula (Ia) are novel pyrazolone derivatives, said derivatives being of the keto form expressed by the following general formula (Ia') and/or of the enol form expressed by another general formula (Ia''):

$$\text{(Ia')}$$

$$\text{(Ia'')}$$

In the above formulae, $R^1$ is a cycloalkyl group of from 5 to 7 carbon atoms such as cyclopentyl group, cyclohexyl group, and cycloheptyl group; a phenyl group which may contain substituent(s); or a pyridyl group.

The substituents for the phenyl group include alkyl groups of from 1 to 5 carbon atoms such as methyl group, ethyl group, propyl group, isopropyl group, butyl group, isobutyl group, sec-butyl group, tert-butyl group, pentyl group, etc.; alkoxy groups of from 1 to 5 carbon atoms such as methoxy group, ethoxy group, propoxy group, isopropoxy group, butoxy group, pentyloxy group, etc.; halogen atoms such as chlorine atom, etc., alkoxycarbonyl groups of from 2 to 5 total carbon atoms such as methoxycarbonyl group, ethoxycarbonyl group, propoxycarbonyl group, butoxycarbonyl group, etc.; carboxyl group; alkoxycarbonylalkyl groups such as alkoxycarbonylmethyl groups of from 3 to 6 total carbon atoms; carboxyalkyl groups such as carboxymethyl group; alkylmercapto groups of from 1 to 3 carbon atoms such as methylmercapto group, ethylmercapto groups, propylmercapto group, etc.; trifluoromethyl group; hydroxyl group and the like.

$R^2$ represents a hydrogen atom (H) or an alkyl group of from 1 to 5 carbon atoms.

$R^3$ represents a pyridyl group, a furanyl group, or an imidazolyl group.

n represents zero (0) or one (1).

In the compounds of the formulae (Ia), (Ia') and (Ia") of the present invention, it is preferable that $R^1$ is a cyclohexyl group, a phenyl group, a 4-methylphenyl group, a 4-ethylphenyl group, a 4-methoxyphenyl group, a 4-ethoxyphenyl group or a 4-chlorophenyl group, $R^2$ is a hydrogen atom (H), a methyl group, an ethyl group or a propyl group, and $R^3$ is a pyridyl group or a furanyl group. Particularly preferred compounds contain a 4-methylphenyl group or a 4-chlorophenyl group as $R^1$, a hydrogen atom (H), a methyl group, an ethyl group or a propyl group as $R^2$, and a pyridyl group as $R^3$.

Among salts of the compounds as expressed by the formula (I), those which are pharmaceutically acceptable and are therefore used in the composition of the present invention include salts with mineral acids such as hydrochloric acid, sulfuric acid, hydrobromic acid, phosphoric acid, etc.; salts with organic acids such as methanesulfonic acid, p-toluenesulfonic acid, benzenesulfonic acid, acetic acid, glycolic acid, glucuronic acid, maleic acid, fumaric acid, oxalic acid, ascorbic acid, citric acid, salicylic acid, nicotinic acid, tartaric acid, etc.; salts with alkali metals such as sodium, potassium, etc.; salts with alkaline earth metals such as magnesium, calcium, etc.; and salts with amines such as ammonia, tris-(hydroxymethyl)aminomethane, N,N-bis-(hydroxyethyl)piperazine, 2-amino-2-methyl-1-propanol, ethanolamine, N-methyl glucamine, L-glucamine, etc.

The compounds of the present invention can be synthesized by arbitrary processes meeting the purpose of the invention, one example of which is shown as follows:

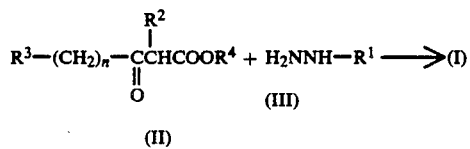

wherein $R^1$, $R^2$, $R^3$ and n are as previously defined, and $R^4$ represents an alkyl group of from 1 to 5 carbon atoms.

In more detail, the compound as expressed by the formula (I) is obtained by making a β-keto-acid derivative as expressed by the formula (II) to react with a hydrazine derivative as expressed by the formula (III) at a temperature in the range of 10° to 200° C. in the presence or absence of a solvent selected from alcohols such as methanol and ethanol and aromatic hydrocarbons such as benzene and toluene, using when necessary a catalyst selected from bases such as potassium carbonate, sodium ethoxide, potassium-t-butoxide, sodium hydroxide, potassium hydroxide, sodium acetate, etc.; mineral acids such as hydrochloric acid, sulfuric acid, hydrobromic acid, etc.; and organic acids such as acetic acid, p-toluenesulfonic acid, etc.

In addition, the intended compound as expressed by the formula (I) can be synthesized in the following way, depending upon the substituent(s) on the phenyl group of $R^1$:

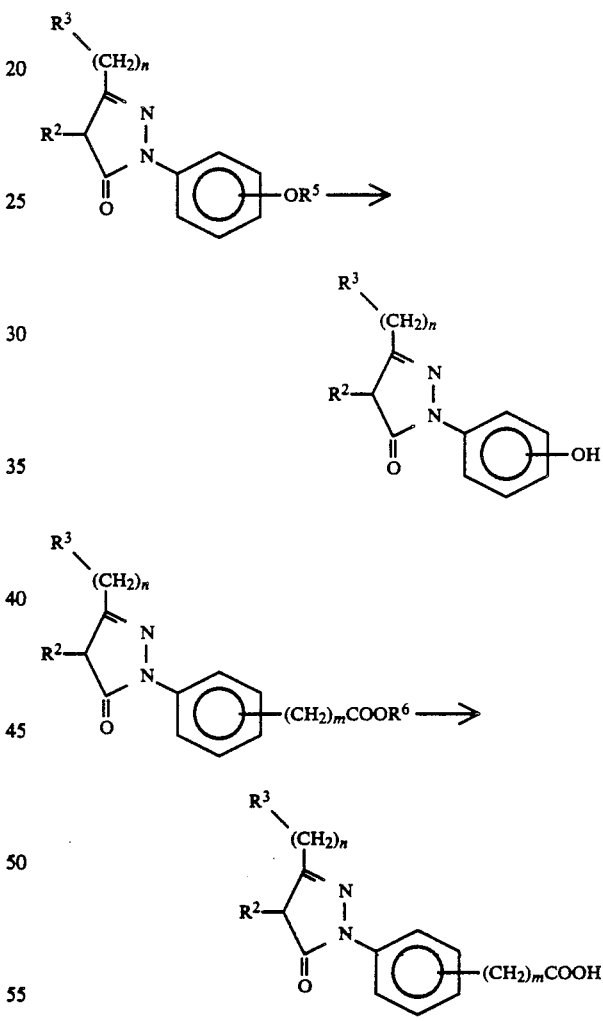

wherein $R^1$, $R^2$, $R^3$ and n have the aforestated meanings, respectively, both $R^5$ and $R^6$ are alkyl groups of from 1 to 5 carbon atoms, respectively, and m represent zero (0) or one (1).

Furthermore, the intended compound of the formula (I) wherein said substituent is a hydroxyl group can be obtained by splitting the relevant alkoxy group with hydrobromic acid, a Lewis acid or the like.

Moreover, in case of said substituent being a carboxyl group or a carboxymethyl group, the intended compound can be obtained by hydrolyzing the alkoxycarbonyl group or the alkoxycarbonylmethyl group under the conventional reaction conditions such as in the presence of an alkali or an acid.

The synthetic methods of the compounds of the formula (Ia) need no particular explanation because these constitute part of the compounds of the formula (I).

In applying the compound of the formula (I) to clinical use, it is preferable that a compound of the formula (I) be dosed to an adult from 1 to 3 times per day, each time in an amount of from 1 to 100 mg for oral administration, from 2 to 5 times per day, each time in an amount of from 0.01 to 10 mg for intravenous injection, or in an amount of the sum of the above for continuous intravenous drip infusion, and from 1 to 3 times per day, each time in an amount of from 1 to 100 mg for rectum dosing. However, it is more preferable that the above standard dose be increased or decreased case by case depending upon the age, morbid state and the condition of disease.

In addition sustained release preparations may be applied for oral or rectum dosing.

In preparing the compositions of the present invention, at least one of the compounds the formula (I) and their pharmaceutically acceptable salts is usually used, together with an ordinary pharmaceutical carrier, filler or other appropriate additives.

The pharmaceutical carrier ma be in the form of solid or liquid. Examples of solid carriers are lactose, kaoline, cane sugar, crystalline cellulose, corn starch, talc, agar-agar, pectin, acacia, stearic acid, magnesium stearate, lecithin, sodium chloride and the like. Examples of liquid carriers are syrup, glycerol, arachis oil, polyvinyl pyrrolidone, olive oil, ethanol, benzyl alcohol, propylene glycol, water, etc.

The compositions of the present invention may take a variety of preparation forms. In the case of solid carriers, the compositions of the present inventions may be prepared as tablets, powders, granules, soft-capsules, hard-capsules, gelatin-capsules, sappositories or troches. The amount of the solid carrier is variable in a wide range but preferably ranges from about 1 mg to about 1 g. In the case of liquid carriers, the compositions can be prepared as syrup, milky liquid, soft-gelatin capsules, sterilized injectable liquid in an ampule, or aqueous or nonaqueous suspension.

The compounds of the formula (I) can be in the form where they are included in cyclodextrin molecules or contained in liposomes.

D. Effect of the Invention

Having excellent function, the lipid-peroxide formation inhibiting compositions of the present invention are useful as a preventive medicine and/or therapeutic medicine for various ischemic diseases or various diseases attributable to the same, that is, various brain diseases such as cerebral vascular diseases such as cerebral infarction, cerebral apoplexy, etc., cerebral depression due to the above diseases, vascular dementia, morbid change in cerebral vascular tissue due to aging, etc., various heart diseases such as cardiac infarction, cardiac insufficiency, etc., resulting from ischemia in myocardia, and various peripheral circulatory diseases.

E. Examples

Specific embodiments of the present invention are illustrated by the following examples. It should be understood, however, that the present invention is not confined to the specific limitations set forth in the individual examples unless departing from the spirit and scope of the present invention. The compounds specified by the compound numbers in the examples refer to those in Table 1.

Synthesis Example 1

Synthesis of 1-phenyl-3-(3-pyridyl)-2-pyrazolin-5-one (Compound No.1)

To 15 ml of ethanol were added by 3.86 g of ethyl 3-oxo-3-(3-pyridyl) propionate and 2.16 g of phenylhydrazine and stirred for 2 hours at 50° to 60° C. After allowing to cool, the deposited crystals were filtrated off and recrystallized from ethanol to obtain 2.83 g of Compound No. 1 as colorless crystals.
Yield: 60%,
Melting point: 200°–204° C.

Synthesis Examples 2–54

Synthesis of Compounds Nos. 2–8, 11–47 and 51–59

As in the case with Synthesis Example 1, Compounds Nos. 2–8, 11–47, and 51–59 as shown in Table 1 were synthesized.

Synthesis Example 55

Synthesis of 4-[3-(3-pyridyl)-5-oxo-2-pyrazolin-1-il]phenylacetic acid (Compound No. 9)

To 1.6 ml of aqueous 5% sodium-hydroxide solution was added 323 mg of 1-(4-ethoxycarbonyl methylphenyl)-3-(3-pyridyl)-2-pyrazolin-5-one and stirred for 1 hour at room temperature. After adjusting the pH value of the reaction mixture to 3 with 2% hydrochloric acid (HCl), the deposited crystals were filtrated to obtain 182 mg of 4-[3-(3-pyridyl)-5-oxo-2-pyrazolin-1-il]phenylacetic acid as colorless crystals.
Yield: 62%,
Melting point: >250° C.

Synthesis Example 56

Synthsis of 4-[3-(1-imidazolylmethyl)-5-oxo-2-pyrazolin-1-yl]phenylacetic acid (Compound No. 48)

To 0.5 ml of aqueous 5% sodium hydroxide solution was added 100 mg of 1-(4-ethoxycarbonylmethylphenyl)-3-(1-imidazolylmethyl)-2-pyrazolin-5-one and stirred at room temperature for one hour.

The reaction mixture was adjusted in pH to 3 with 2% hydrochloric acid and the precipitated crystals were collected by filtering. 60 mg of Compound No. 48 was obtained as colorless crystals.
Yield: 65%,
Melting point: 220°–225° C.

Synthesis Example 57

Synthesis of Compound No. 49

As in Synthesis Example 56, Compound No. 49 was synthesized.

Synthesis Example 58

Synthesis of 1-(4-hydroxyphenyl)-3-(3-pyridyl)-2-pyrazolin-5-one (Compound No. 10)

To a mixture of 1 ml of 47% hydrobromic acid and 1 ml of acetic acid was added 267 mg of 1-(4-methoxyphenyl)-3-(3-pyridyl)-2-pyrazolin-5-one and stirred under reflux for 6 hours. After distilling off the solvent, water and aqueous NaHCO$_3$ solution were added to the residue to adjust the pH value to 4 and extraction was made using ethyl acetate. After drying and concentrating the organic layer, the residue was recrystallized from ethanol to obtain 162 mg of Compound No. 10 as colorless crystals.
Yield: 64%,
Melting point: >250° C.

Synthesis Example 59

Synthesis of 1-(4-hydroxyphenyl)-3-(1-imidazolylmethyl)-2-pyrazolin-5-one (Compound No. 50)

To a mixture of 1 ml of 47% hydrobromic acid and 1 ml of acetic acid was added 100 mg of 3-(1-imidazolylmethyl)-2-pyrazolin-5-one and stirred under reflux for 4 hours. After removing the solvent by evaporating, the residue was adjusted in pH to 4 by adding water and an aqueous NaHCO$_3$ solution and then extracted with a mixed solvent of chloroform and ethanol (4:1).

The organic layer was dried and concentrated. Recrystallization of the residue from ethanol-ether gave 49 mg of Compound No. 50 as colorless crystals.
Yield: 60%,
Melting point: 168°-170° C.

Application Example (1) Lipid-peroxide formation inhibiting activity (a) Preparation of cerebral homogenate Cerebral homogenate was prepared according to the following procedure, using a Wistar strain male rat: The rat was subjected to chest opening under anesthesia by dosing 45 mg/kg, i.p. of pentobarbital sodium in abdomen, and a polyethylene tube was inserted into the aorta through the left atrium and fixed. Then, cerebral irrigation was made with ice-cold physiological saline solution buffered with 50 mM phosphoric acid (pH value of 7.4, hereinafter referred to as "PBS"), and the whole brain was extracted. After removing the cerebellum, the cerebrum was weighed in the wet state, added with PBS of 9 times the weight and homogenized in ice-cold water with a teflon homogenizer. The cerebral homogenate was centrifuged at 40° C. and 2200 rpm for 10 minutes, and 0.3 ml of the supernatant was partitioned into a ground stoppered light-resistant test tube to prepare a cerebral homogenate to be used for drug evaluation.

(b) Evaluation of test drug

The cerebral homogenate which was prepared by the above procedure (a) was added with 0.6 ml of PBS and 10 μl of ethanol solution which contained the test drug of 0.3 to 100 μl in final concentration and incubated for 30 minutes in a water bath at 37° C. Then, the mixture was added with 200 μl of aqueous 35% solution of perchloric acid and centrifuged at 4° C. and 2,600 rpm for 10 minutes to collect the supernatant.

In addition, 10 μl of ethanol (blank) was added instead of the test drug.

(c) Determination of lipid peroxide

The supernatant of 0.1 ml which was obtained in the above procedure (b) was added with 0.2 ml of aqueous 8.1% sodium dodecyl sulfate solution, 1.5 ml of 20% acetic acid buffer solution (pH of 3.5), 1.5 ml of 0.67% 2-thiobarbituric acid solution and 0.7 ml of distilled water and mixed. The mixed solution was heated for 60 minutes in boiling water bath, quenched with ice-cold water and added with 1.0 ml of distilled water and 5.0 ml of a mixture solution of pyridine and butanol (1:15). After 30 seconds of shaking, the mixed solution was centrifuged at 3000 rpm for 10 minutes, and the supernatant was collected as the sample for lipid peroxide measurement.

In addition, 0.1 ml of Lipoperoxide-test reagent (Wako Pure Chemicals Co., Ltd.: 1,1,3,3-tetraethoxypropane is contained by 5 mmole/ml) was added instead of the cerebral homogenate obtained in the above procedure (b) to prepare the reference solution.

The amount of lipid peroxide was measured at a excitation wavelength of 515 nm and a fluorescence wavelength of 550 nm using a fluoro-spectrophotometer (Model 204, made by Hitachi, Ltd.) and calculated by the following formula:

$$\text{Lipid peroxide amount } (TBA \text{ value}) = 0.5 \times \frac{f}{F} \times \frac{1.1}{0.3} \times 10 \text{ (nmole/ml)}$$

where,
F = fluorescence intensity of the reference solution
f = fluorescence intensity of the test drug.

Then, the inhibition rates of the test drugs at each concentration were obtained for the TBA value of the blank under (b) above and IC$_{50}$ value were calculated by the method of least square means. The results are shown in Table 1.

(2) Cerebral protective activity in cerebral ischemia model:

A Wistar-strain male rat weighing about 400 g was intramuscularly dosed with 0.6 mg of d-tubocurarine to immobilize. After inserting a trachea cannula, the head was fixed to the stereofaxic apparatus under artificial respiration. After incising the head skin and drilling the cranial bone, an electrode for recording electroencephalogram was placed on the surface of the left frontal cortex. After fixing the electrode to the cranial bone using dental cement, the rat was supported in the rear position. Then, a cannula for measuring the blood pressure was intubated to the left femoral artery and another cannula for additionally dosing d-tubocurarine was also intubated to the left femoral vein. The heart rate was measured by a cardiotachometer triggered by pulse pressure.

After reaching the stable state of several parameters including blood pressure, heart rate and electroencephalogram, the effective ingredient of the present invention which was previously prepared so as to form suspension of 1 ml/kg with 1% tragacanth gum solution was directly dosed into the duodenum in a dose of 10 mg/kg at 30 minutes before cerebral ischemia loading. The control group were dosed by the same volume of 1% tragacanth gum solution only.

The blood pressure, heart rate and electroencephalogram were monitored 10 to 20 minutes after drug dosing with the multipurpose polygraph (Model RM-85, made by Nihon Kohden Co., Ltd.), and operation was made according to the following procedure:

Firstly, the ribs were freed from the left costal cartilage and the chest was opened. Then, 30 minutes after drug dosing, the left common carotid artery, left vertebral artery and brachiocephalic artery were simultaneously plugged at the origin of the arteries with artery clips to stop the blood flow into the brain for 10 minutes.

The resumption of blood flow into the brain was conducted by simultaneously releasing the artery clips which were attached to said positions.

The cerebral protective activity of the drug against the disturbance after the release of cerebral ischemic load was investigated by the restoration of electroencephalogram.

During the experiment, the rectal temperature was maintained at 37°-38° C. with a heating pad and continuously recorded on the recorder along with electroencephalogram, femoral blood pressure and heart rate.

Immediately after loading cerebral ischemia for 10 minutes, the voltage of electroencephalogram was lowered and, disappeared after 15 seconds in average. Such flattening change of electroencephalogram during the ischemic loading was observed in both the control group and the group which was given the effective ingredient of the present invention.

Even after releasing the cerebral ischemia of 10 minutes, the appearance of electroencephalogram was not recognized at all in the control group and the levelling proceeded in the same mode as in the ischemic loading. The continuous levelling led to the death of the animals used as control after 75 minutes in average from the blood reflow.

As opposed to the above result, however, in regard to the group which was given the effective ingredient of the compounds No. 1 or No. 24 of the present invention, the electroencephalogram appeared with restoration during the releasing, and the function of the pulsation system was activated and normalized along with the restoration of cerebral function. As the overall result, the survival period of time of the animals of the group was clearly extended.

Formulation Examples

The lipid-peroxide formation inhibiting compositions of the present invention were prepared as follows;

(1) Tablet

The following components were mixed according to the ordinary way and tableted with the customary equipment:
Compound No. 1 10 mg,
Crystalline celullose 21 mg,
Corn startch 33 mg,
Lactose 65 mg, and
Magnesium stearate 1.3 mg.

(2) Soft capsule

The following components were mixed according to the ordinary way and packed in a soft capsule:
Compound No. 1 10 mg,
Olive oil 105 mg, and
Lecithin 6.5 mg.

(3) In-ampule injection

The following components were mixed according to the ordinary way to prepare a 1 ml ampule:
Compound No. 1 0.7 mg,
Sodium chloride 3.5 mg, and
Distilled water for injection 1.0 ml.

TABLE 1

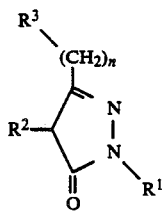

| Compound No. | $R^1$ | $R^2$ | $R^3$ | n | Melting Point (°C.) | $IC_{50}$ Value(μM) |
|---|---|---|---|---|---|---|
| 1 | –C$_6$H$_5$ | H | pyridyl | 0 | 200-204 | 23.6 |
| 2 | –C$_6$H$_4$–CH$_3$ | " | " | " | 185-186 | 10.3 |
| 3 | –C$_6$H$_4$–CH$_2$CH$_3$ | " | " | " | 213-215 | 4.0 |
| 4 | –C$_6$H$_4$–OCH$_3$ | " | " | " | 173-174 | 37.0 |

TABLE 1-continued
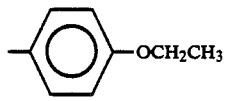
| Compound No. | R¹ | R² | R³ | n | Melting Point (°C.) | IC$_{50}$ Value(μM) |
|---|---|---|---|---|---|---|
| 5 |  —OCH$_2$CH$_3$ | " | " | " | 209.5–210.5 | 12.9 |
| 6 | 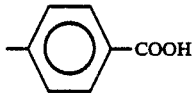 —Cl | " | " | " | 183–185 | 4.3 |
| 7 | 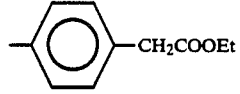 —COOH | " | " | " | >250 | (1.9%)*³ |
| 8 | 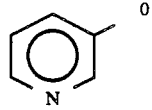 —CH$_2$COOEt | H | 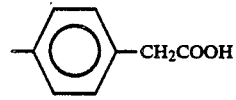 | 0 | 106–107 | 13.6 |
| 9 | 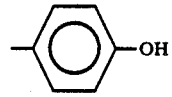 —CH$_2$COOH | " | " | " | >250 | (2.6%)*³ |
| 10 | 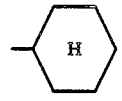 —OH | " | " | " | >250 | 102.4 |
| 11 | 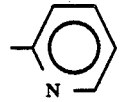 H | " | " | " | 219.5–220.5 | 16.9 |
| 12 |  | " | " | " | 122–123 | (43.2%)*³ |
| 13 | 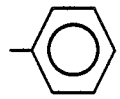 | " | " | " | 204–205 | 84.1 |
| 14 | 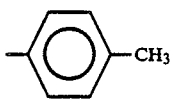 | CH$_3$— | " | " | 141–142 | 38.9 |
| 15 | 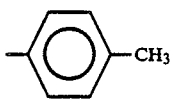 —CH$_3$ | " | " | " | 188–189 | 12.5 |

TABLE 1-continued
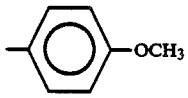
| Compound No. | R¹ | R² | R³ | n | Melting Point (°C.) | IC$_{50}$ Value(μM) |
|---|---|---|---|---|---|---|
| 16 | 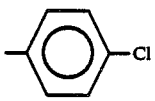 | " | " | " | 201–202.5 | 46.3 |
| 17 | 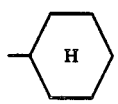 | " | " | " | 174.5–175.5 | 7.1 |
| 18 | 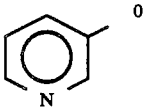 | CH$_3$— | 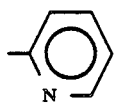 | 0 | 157–158 | 29.3 |
| 19 | 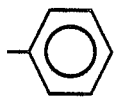 | " | " | " | 137.5–138.5 | 12.3 |
| 20 | 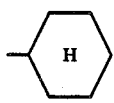 | CH$_3$CH$_2$— | " | " | 132–140*[1] | 29.4 |
| 21 | 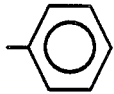 | " | " | " | 244–244.5 | (1.0%)*[3] |
| 22 | 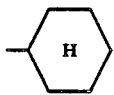 | CH$_3$CH$_2$CH$_2$— | " | " | 110–112 | 28.2 |
| 23 | 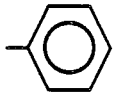 | " | " | " | 243–250*[2] | (46.1%)*[3] |
| 24 | 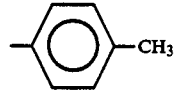 | H | " | 1 | 124–126 | 16.4 |
| 25 | 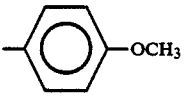 | " | " | " | 164.5–166 | 7.4 |
| 26 |  | " | " | " | 159–161 | 23.6 |

TABLE 1-continued
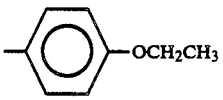
| Compound No. | R¹ | R² | R³ | n | Melting Point (°C.) | IC$_{50}$ Value(μM) |
|---|---|---|---|---|---|---|
| 27 | 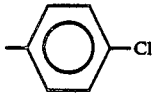 | " | " | " | 138.5–140 | 12.2 |
| 28 | 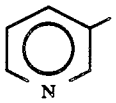 | H | 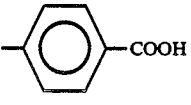 | 1 | 161–163 | 4.1 |
| 29 | 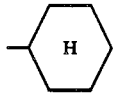 | H | " | " | 194–195 | (17.6%)*³ |
| 30 | 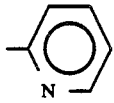 | H | " | " | 155–156 | 24.0 |
| 31 | 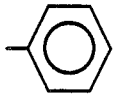 | H | " | " | 80–81 | 6.2 |
| 32 | 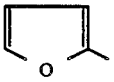 | H | 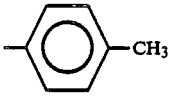 | 0 | 177–178 | 4.3 |
| 33 | 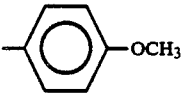 | H | " | " | 149.5–151 | 4.1 |
| 34 | 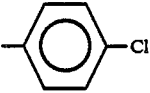 | H | " | " | 99–100 | 6.5 |
| 35 | 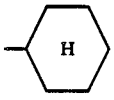 | H | " | " | 142.5–145 | 3.7 |
| 36 | 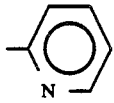 | H | " | " | 195–197 | 8.3 |
| 37 | 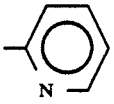 | H | " | " | 94.5–96.5 | 15.4 |

TABLE 1-continued

[Structure: pyrazolone with R³-(CH₂)ₙ at 5-position, R² at 4-position, N-N-R¹, C=O]

| Compound No. | R¹ | R² | R³ | n | Melting Point (°C.) | IC₅₀ Value(μM) |
|---|---|---|---|---|---|---|
| 38 | phenyl | H | imidazol-1-yl | 1 | 172–175 | 60.1 |
| 39 | 4-CH₃-phenyl | " | " | " | 210–212 | 43.0 |
| 40 | cyclohexyl | " | " | " | 171–172 | (39.4%)*³ |
| 41 | 3-CH₃-phenyl | " | " | " | 177–178 | 60.0 |
| 42 | 4-CH₂CH₃-phenyl | " | " | " | 220–221 | 24.4 |
| 43 | 4-OCH₃-phenyl | " | " | " | 212–213.5 | (30.2%)*³ |
| 44 | 4-Cl-phenyl | " | " | " | 207–208 | 22.7 |
| 45 | 3,4-diCl-phenyl | " | " | " | 194–195.5 | 11.0 |
| 46 | 4-CH₂COOEt-phenyl | " | " | " | 195–198 | 60.5 |
| 47 | 4-COOEt-phenyl | " | " | " | 208–209.5 | 35.1 |
| 48 | 4-CH₂COOH-phenyl | H | imidazol-1-yl | 1 | 220–225 | (0.5%)*³ |

TABLE 1-continued
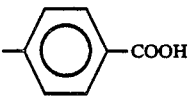
| Compound No. | R¹ | R² | R³ | n | Melting Point (°C.) | IC$_{50}$ Value(μM) |
|---|---|---|---|---|---|---|
| 49 | 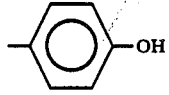 | " | " | " | 264–265 | (12.9%)*3 |
| 50 | 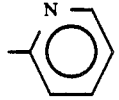 | " | " | " | 168–170 | (14.7%)*3 |
| 51 | 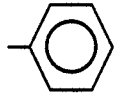 | " | " | " | 110.5–112 | 51.3 |
| 52 | 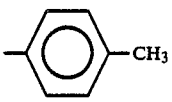 | CH$_3$CH$_2$— | " | " | 148–149*2 | (4.3%)*3 |
| 53 | 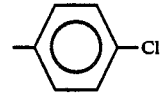 | " | " | " | 95–98*1 | 38.2 |
| 54 | 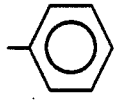 | " | " | " | 189–190 | 37.8 |
| 55 | 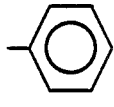 | CH$_3$\CH—/CH$_3$ | " | " | 205–206.5 | (27.3%)*3 |
| 56 | 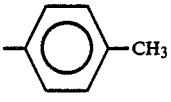 | CH$_3$CH$_2$CH$_2$CH$_3$— | " | " | 150–151 | (47.7%)*3 |
| 57 | 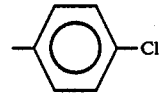 | " | " | " | 168–169 | 35.9 |
| 58 | 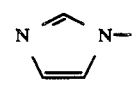 | CH$_3$CH$_2$CH$_2$CH$_3$— | N⌒N— | 1 | 164–164.5 | 27.9 |

TABLE 1-continued

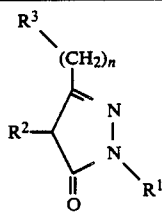

| Compound No. | $R^1$ | $R^2$ | $R^3$ | n | Melting Point (°C.) | $IC_{50}$ Value(μM) |
| --- | --- | --- | --- | --- | --- | --- |
| 59 | 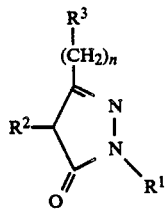 H | " | | " | Amorphous | 25.9 |

*[1]Hydrochloride
*[2]Fumaric Acid Salt
*[3]Percent inhibition at 100 μM

What is claimed is:

1. A pyrazolone derivative of the following general formula:

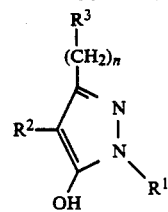

wherein $R^1$ represents a pyridyl group, $R^2$ is a hydrogen atom or an alkyl group, and $R^3$ is a pyridyl group and n is zero or one, or a pharmaceutically acceptable salt thereof.

* * * * *